United States Patent
Forbes

(10) Patent No.: US 11,913,951 B2
(45) Date of Patent: Feb. 27, 2024

(54) HIGH THROUGHPUT METHOD FOR MEASURING THE PROTEASE ACTIVITY OF COMPLEMENT C3 CONVERTASE

(71) Applicant: Alexion Pharmaceuticals, Inc., Boston, MA (US)

(72) Inventor: Christen D. Forbes, North Haven, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 560 days.

(21) Appl. No.: 16/981,008

(22) PCT Filed: Mar. 21, 2019

(86) PCT No.: PCT/US2019/023373
§ 371 (c)(1),
(2) Date: Sep. 15, 2020

(87) PCT Pub. No.: WO2019/190877
PCT Pub. Date: Oct. 3, 2019

(65) Prior Publication Data
US 2021/0025886 A1    Jan. 28, 2021

Related U.S. Application Data

(60) Provisional application No. 62/648,122, filed on Mar. 26, 2018.

(51) Int. Cl.
*G01N 33/564* (2006.01)
*G01N 33/542* (2006.01)

(52) U.S. Cl.
CPC ......... *G01N 33/564* (2013.01); *G01N 33/542* (2013.01); *G01N 2333/4716* (2013.01)

(58) Field of Classification Search
CPC ............... G01N 33/564; G01N 33/542; G01N 2333/4716
See application file for complete search history.

(56) References Cited

U.S. PATENT DOCUMENTS 9,291,622 B2 *   3/2016   Zhang ................... C07K 16/18
10,591,481 B2 *  3/2020   Orren .............. C12Y 304/21046
(Continued)

FOREIGN PATENT DOCUMENTS

WO      2010/135717 A2     11/2010
WO      WO-2010135717 A2 * 11/2010 ............. C07K 16/18
(Continued)

OTHER PUBLICATIONS

Janeway et al.(Immunobiology: the Immune System in Health and Disease (2001), Elsevier Science Ltd/Garland Publishing, New York, NY, Fifth Edition, sections 3-6 and 3-7 (Year: 2001).*
(Continued)

*Primary Examiner* — Ann Montgomery
*Assistant Examiner* — Chau N. B. Tran
(74) *Attorney, Agent, or Firm* — Nelson Mullins Riley & Scarborough LLP; Jane E. Remillard, Esq.; Jill Gorny Sloper, Esq.

(57) ABSTRACT

Provided herein are high throughput methods for measuring the protease activity of the complement C3 convertase by detecting the consumption of C3 or the production of C3a in vivo and in vitro.

20 Claims, 9 Drawing Sheets
Specification includes a Sequence Listing.

(56) References Cited

U.S. PATENT DOCUMENTS

| | | |
|---|---|---|
| 2009/0220988 A1 | 9/2009 | Trinquet et al. |
| 2015/0247849 A1* | 9/2015 | Tamburini ............ G01N 33/564 435/7.1 |
| 2018/0087087 A1* | 3/2018 | Johnson ................... C12Q 1/25 |

FOREIGN PATENT DOCUMENTS

| | | | |
|---|---|---|---|
| WO | WO-2014028861 A1 * | 2/2014 | ............ A61B 5/4842 |
| WO | 2016/128689 A1 | 8/2016 | |
| WO | 2016/151557 A1 | 9/2016 | |
| WO | 2017/075170 A1 | 5/2017 | |

OTHER PUBLICATIONS

Wang, Measurement of CAMP for Gαs- and Gαi Protein-Coupled Receptors (GPCRs), NIH, 2017 (Year: 2017).*

Almagro et al. Humanization of Antibodies, Frontiers in Bioscience 13, 1619-1633, 2008 (Year: 2008).*

Goel et al. "Plasticity within the Antigen Combining Site May Manifest as Molecular Mimicry in the Humoral Immune Response", The Journal of Immunology 173(12):7358-7367, 2004 (Year: 2004).*

Edwards et al. The remarkable flexibility of the human antibody repertoire; isolation of over one thousand different antibodies to a single protein, BLyS, J. Mol. Biol. (2003) 334, 103-118, DOI: 10.1016/j.jmb.2003.09.054 (Year: 2003).*

Lloyd et al. Modelling the human immune response: performance of a 10e11 human antibody repertoire against a broad panel of therapeutically relevant antigens, Protein Engineering, Design and Selection, vol. 22, Issue 3, Mar. 1, 2009, pp. 159-168, https://doi.org/10.1093/protein/gzn058 (Year: 2009).*

Brown et al. Tolerance of single, but not multiple, amino acid replacements in antibody VH CDR 2: a means of minimizing B cell wastage from somatic hypermutation?, J Immunol. May 1996;156(9):3285-91 (Year: 1996).*

Vajdos et al. Comprehensive functional maps of the antigen-binding site of an anti-ErbB2 antibody obtained with shotgun scanning mutagenesis, J Mol Biol. Jul. 5, 2002;320(2):415-28, DOI: 10.1016/S0022-2836(02)00264-4 (Year: 2002).*

Abcam (Human complement C3b ELISA kit, 2014) (Year: 2014).*

Lumen Learning Figure 1 see below (https://courses.lumenlearning.com/suny-microbiology/chapter/polyclonal-and-monoclonal-antibody-production/ Oct. 2, 2016) (Year: 2016).*

Almagro & Fransson, Frontiers in Bioscience 2008; 13:1619-33 (Year: 2008).*

Gershoni et al., Epitope Mapping, Biodrugs 2007; 21 (3): 145-156 p. 146 section 1.1 (Year: 2007).*

Blythe et al., Benchmarking B cell epitope prediction: Underperformance of existing methods, Protein Science (2005), 14:246-248 p. 246 (Year: 2005).*

Schreiber et al.,3D-Epitope-Explorer (3DEX): Localization of Conformational Epitopes within Three-Dimensional Structures of Proteins, Wiley Interscience, 42-44, 60596, p. 879 (Year: 2005).*

Wei et al (Development of an open sandwich fluoroimmunoassay based on fluorescence resonance energy transfer, Analytical Biochemistry, vol. 358, Issue 1, 2006, pp. 31-37.). (Year: 2006).*

Wang et al (Measurement of CAMP for Gαs- and Gαi Protein-Coupled Receptors (GPCRs). Nov. 20, 2017. In: Markossian S, Grossman A, Brimacombe K, et al., editors. Assay Guidance Manual [Internet]). (Year: 2017).*

International Preliminary Report on Patentability, PCT/US2019/023373, dated Sep. 29, 2020, 9 pages.

International Search Report and Written Opinion Search, PCT/US2019/023373, dated Jun. 4, 2019, 9 pages.

* cited by examiner

SEQUENCE LISTING

<160> NUMBER OF SEQ ID NOS: 10

<210> SEQ ID NO 1
<211> LENGTH: 10
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Asn Ile Lys Asp Ser Leu Ile His
1               5                   10

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Trp Ile Asp Pro Asp Asp Gly Glu Thr Lys Tyr Ala Pro Lys Phe Gln
1               5                   10                  15

Asp

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Arg Ser Gly Glu Gly Tyr Phe Asp Tyr
1               5

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Arg Ala Ser Gln Ser Ile Ser Asp Tyr Leu His
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ala Ser Gln Ser Ile Ser Gly
1               5

<210> SEQ ID NO 6
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 6

Gln Asn Gly His Ser Phe Pro Leu Thr
1               5

<210> SEQ ID NO 7
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Ser
                20                  25                  30

Leu Ile His Trp Val Lys Gln Arg Pro Glu Gln Gly Leu Glu Trp Ile
            35                  40                  45

Gly Trp Ile Asp Pro Asp Asp Gly Glu Thr Lys Tyr Ala Pro Lys Phe
        50                  55                  60

Gln Asp Lys Ala Thr Ile Thr Ala Asp Thr Ser Ser Asn Thr Ala Tyr
65                  70                  75                  80

Leu Gln Phe Ser Ser Leu Thr Ser Glu Asp Thr Ala Ile Tyr Tyr Cys
                85                  90                  95

Ala Gly Arg Ser Gly Glu Gly Tyr Phe Asp Tyr Trp Gly Gln Gly Thr
                100                 105                 110

Thr Val Thr Val Ser Ser
            115

<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Val Glu Ile Lys
                100                 105
```

```
<210> SEQ ID NO 9
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9
```

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Ser
            20                  25                  30

Leu Ile His Trp Val Lys Gln Arg Pro Glu Gln Gly Leu Glu Trp Ile
        35                  40                  45

Gly Trp Ile Asp Pro Asp Gly Glu Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu Gln Phe Ser Ser Leu Thr Ser Glu Asp Thr Ala Ile Tyr Tyr Cys
                85                  90                  95

Ala Gly Arg Ser Gly Glu Gly Tyr Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 10
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

HIGH THROUGHPUT METHOD FOR MEASURING THE PROTEASE ACTIVITY OF COMPLEMENT C3 CONVERTASE

RELATED INFORMATION PARAGRAPH

This application is a 35 U.S.C. 371 national stage filing of International Application No. PCT/US2019/023373, filed on Mar. 21, 2019, which claims the benefit of the priority date of U.S. Provisional Application No. 62/648,122, filed on Mar. 26, 2018, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Sep. 14, 2020, is named AXJ-243US_Sequence_Listing.txt and is 10,199 bytes in size.

BACKGROUND

The alternative pathway of the complement system plays a role in immunological, inflammatory, coagulation, and neurodegenerative processes. It is implicated in several human diseases such as age-related macular degeneration, sepsis, cancer, paroxysmal nocturnal hemoglobulinuria ("PNH") and atypical hemolytic uremic syndrome ("aHUS"). A complement-directed drug, a therapeutic C5 antibody (Soliris®), is the first approved treatment for PNH and aHUS.

The alternative pathway relies on a series of enzymatic steps culminating in cleavage of the complement component C3 into cleavage products C3a and C3b, and C5 into C5a and C5b, by the C3 and C5 convertases respectively. Regulators of the alternative pathway can, among other things, prevent or facilitate formation and activity of the C3 and C5 convertases.

Methods for studying C3 convertase, including its regulation and activity in vitro and in vivo, often require detection of substrates (C3) or products (C3a, C3b) using Western blotting technology or commercially available ELISAs. However these methods are low throughput, laborious and often unreliable.

Therefore, there is a need for improved methods to study the complement system and identify complement regulators. This, in turn, could aid in the development of new drugs and facilitate discovery of biomarkers for stratifying patient populations, as well as measuring the progression or improvement of complement-mediated diseases.

SUMMARY

The methods disclosed herein solve the problems discussed above by providing high throughput, reliable means for measuring the protease activity of complement C3 convertase as indicated by the consumption of C3 or production of C3a in vivo and in vitro.

In one aspect, the method comprises detecting C3a in a biological sample by (a) incubating the biological sample with a first and second antibody that bind to human C3a, wherein the first, but not the second, antibody binds to a neoepitope, and wherein the antibodies are FRET pairs; and (b) performing fluorescence resonance energy transfer (FRET) to detect the FRET signal, thereby detecting C3a in the biological sample. In one embodiment, the method further comprises repeating steps (a) and (b) over a time course. In another embodiment, the method further comprises (c) quantifying the amount of C3a in the biological sample by comparing the FRET signal to a standard curve. In yet another embodiment, the method further comprises repeating steps (a), (b), and (c) over a time course.

In another aspect, the method comprises detecting C3 in a biological sample by (a) incubating the biological sample with a first and second antibody that bind to human C3, wherein the first antibody binds to an epitope on C3a and the second antibody binds to an epitope on C3b, and wherein the antibodies are FRET pairs; and (b) performing fluorescence resonance energy transfer (FRET) to detect the FRET signal, thereby detecting C3 in the biological sample. In one embodiment, the method further comprises repeating steps (a) and (b) over a time course. In another embodiment, the method further comprises (c) quantifying the amount of C3 in the biological sample by comparing the FRET signal to a standard curve. In yet another embodiment, the method further comprises repeating steps (a), (b), and (c) over a time course.

In another embodiment, at least one of the first and second antibodies binds to an epitope recognized by an antibody having the heavy chain variable region comprising the amino acid sequence of SEQ ID NO: 7 and a light chain variable region comprising the amino acid sequence of SEQ ID NO: 8.

In another embodiment, at least one of the first and second antibodies comprises the heavy chain CDR1, CDR2, and CDR3 amino acid sequences set forth in SEQ ID NOs: 1, 2, and 3, respectively, and the light chain CDR1, CDR2, and CDR3 amino acid sequences set forth in SEQ ID NOs: 4, 5, and 6, respectively.

In yet another embodiment, at least one of the first and second antibodies comprises the heavy chain variable region amino acid sequence set forth in SEQ ID NO: 7 and the light chain variable region amino acid sequence set forth in SEQ ID NO: 8.

In one embodiment, one of the first and second antibodies is labeled with a donor fluorophore, and the other of the first and second antibodies is labeled with an acceptor fluorophore. In a particular embodiment, the donor fluorophore is terbium cryptate dye. In another particular embodiment, the acceptor fluorophore is d2 dye.

In one embodiment, the donor fluorophore is excited at 300-600 nm. In another embodiment, the signal from the donor fluorophore is measured at 400-700 nm. In another embodiment, the signal from the acceptor fluorophore is measured at 400-700 nm. In one embodiment, the antibodies bind within 10-100 Å of each other. In another embodiment, the antibodies bind within 50-90 Å of each other.

In a particular embodiment, the FRET is time-resolved fluorescence energy transfer (TR-FRET).

In another embodiment, the method further comprises treating the biological sample with a convertase prior to step (a). In another embodiment, the method further comprises treating the biological sample with cobra venom factor, factor B, and factor D prior to step (a).

In another embodiment, the biological sample is human serum, plasma, cell supernatant, cell lysate, or urine. In another embodiment, the biological sample is from a human patient suffering from a complement-related disease. In yet another embodiment, the biological sample is from a human patient suffering from lupus nephritis, dense deposit disease, C3 glomerulonephritis, IgA nephropathy, membranous nephropathy, COPD, or asthma.

DETAILED DESCRIPTION

I. Definitions

Figure 1A:
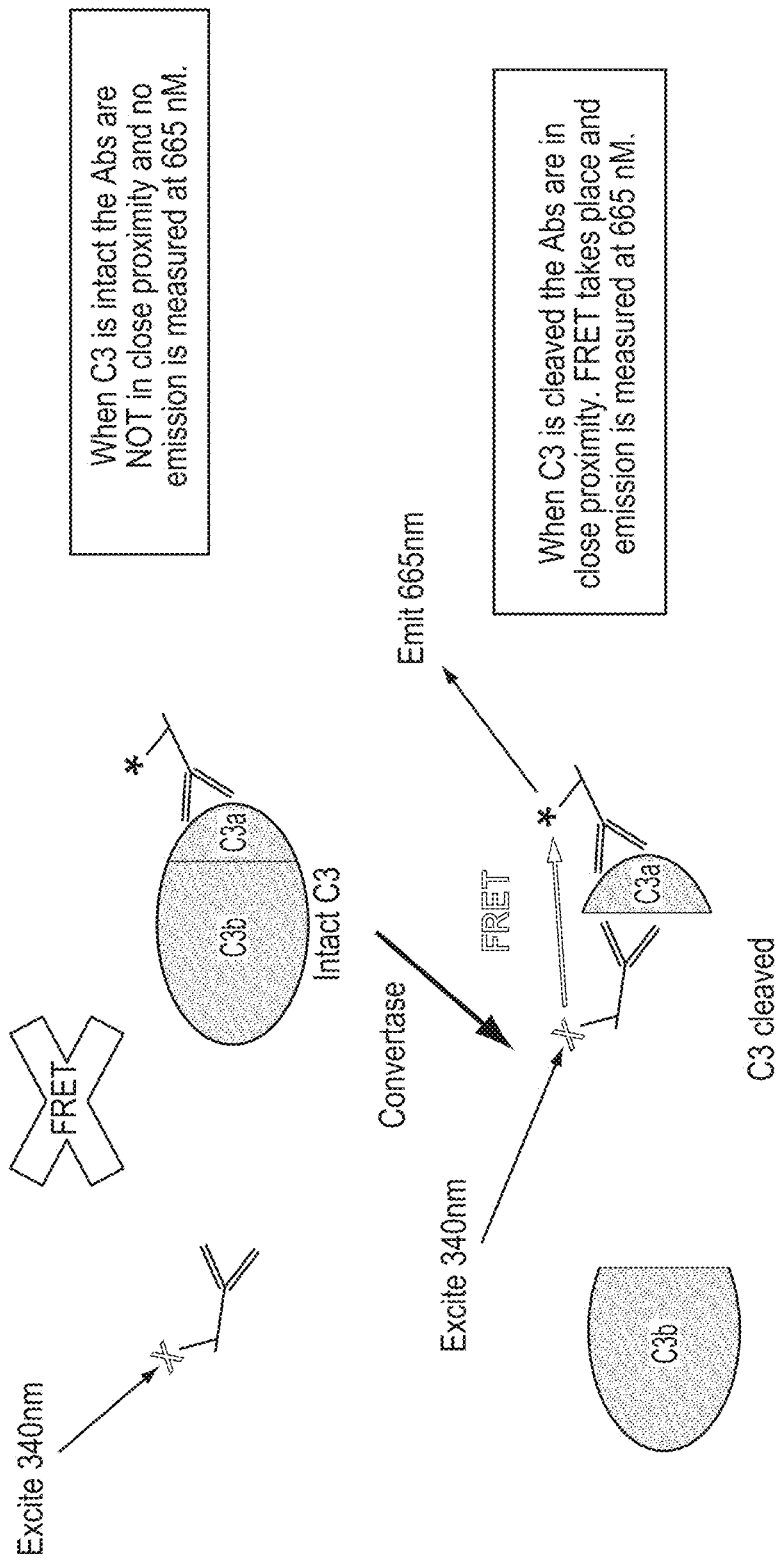
FIGS. 1A and 1B are schematic diagrams of a method to detect C3a and C3, respectively, using FRET.

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of immunology, protein chemistry, biochemistry, recombinant DNA techniques, and pharmacology are employed.

The term "antibody" as used herein refers to polypeptides comprising at least one antibody derived antigen binding site (e.g., VH/VL region or F$_v$, or CDR), and includes whole antibodies and any antigen binding fragments (i.e., "antigen-binding portions") or single chains thereof. Antibodies include known forms of antibodies. For example, the antibody can be a human antibody, a humanized antibody, a bispecific antibody, or a chimeric antibody. A whole "antibody" refers to a glycoprotein comprising at least two heavy (H) chains and two light (L) chains inter-connected by disulfide bonds, in which each heavy chain is comprised of a heavy chain variable region (abbreviated herein as V$_H$) and a heavy chain constant region; and each light chain is comprised of a light chain variable region (abbreviated herein as V$_L$) and a light chain constant region. The V$_H$ and V$_L$ regions can be further subdivided into regions of hypervariability, termed complementarity determining regions (CDR), interspersed with regions that are more conserved, termed framework regions (FR). Each V$_H$ and V$_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The exact boundaries of CDRs can be defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, MD]. In such cases, the CDRs can be referred to as "Kabat CDRs" (e.g., "Kabat LCDR2" or "Kabat HCDR1"). In other embodiments, the positions of the CDRs of a light or heavy chain variable region can be as defined by Chothia et al. (1989) Nature 342:877-883. Accordingly, these regions can be referred to as "Chothia CDRs" (e.g., "Chothia LCDR2" or "Chothia HCDR3"). In other embodiments, the positions of the CDRs of the light and heavy chain variable regions can be as defined by a Kabat-Chothia combined definition. In such embodiments, these regions can be referred to as "combined Kabat-Chothia CDRs". Thomas et al. [(1996) Mol Immunol 33(17/18):1389-1401] exemplifies the identification of CDR boundaries according to Kabat and Chothia definitions. In other embodiments, the positions of the CDRs or framework regions within a light or heavy chain variable domain can be as defined by the international ImMunoGeneTics database (IMGT) standard. Marie-Paule Lefranc et al. [(2003) Developmental & Comparative Immunology 27(1):55-77] exemplifies the identification of and CDR boundaries according to IMGT standard. Accordingly, these regions can be referred to as "IMGT CDRs" (e.g., "IMGT-LCDR2" or "IMGT-HCDR3").

The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered by a protein engineering technique (e.g., by mutation, deletion, substitution, and/or conjugation to a non-antibody moiety). For example, an antibody may include one or more variant amino acids (compared to a naturally occurring antibody) which change a property (e.g., a functional property) of the antibody. For example, numerous such alterations are known in the art which affect, e.g., half-life, effector function, and/or immune responses to the antibody in a patient. The term antibody also includes artificial or engineered polypeptide constructs which comprise at least one antibody-derived antigen binding site.

The term "human antibody," as used herein, is intended to include antibodies having variable regions in which both the framework and CDR regions are derived from human germline immunoglobulin sequences as described, for example, by Kabat et al. (See Kabat, et al. (1991) Sequences of proteins of Immunological Interest, Fifth Edition, U.S. Department of Health and Human Services, NIH Publication No. 91-3242).

The term "antigen-binding portion" of an antibody (or simply "antibody portion"), as used herein, refers to one or more fragments of an antibody that retain the ability to specifically bind to an antigen (e.g., CD200), e.g., a Fab, Fab'2, ScFv, SMIP, AFFIBODY® antibody mimetic (Affibody AB AKTIEBOLAG, Sweden), nanobody, or a domain antibody. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). In one embodiment, the composition contains an antigen-binding portions described in U.S. Pat. Nos. 6,090,382 and 6,258,562, each incorporated by reference herein.

The term "monoclonal antibody," refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method. The monoclonal antibodies to be used in accordance with the formulations disclosed herein may be made by the hybridoma method first described by Kohler, et al. (1975) *Nature* 256: 495 or other methods known in the art. A "polyclonal antibody" is an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

The term "biological sample" refers to any sample taken from a human patient. Suitable biological samples for use in the methods described herein include whole blood (or a fraction thereof), serum, plasma, cell supernatant, cell lysate, or urine. A biological sample can be further fractionated, if desired, to a fraction containing particular analytes (e.g., proteins) of interest. For example, a whole blood sample can be fractionated into serum or into fractions containing particular types of proteins.

Biological samples to be tested using the methods of the invention may include fresh or frozen samples collected from a subject, or archival samples with known diagnosis, treatment and/or outcome history. The biological samples can be obtained from a subject, e.g., a subject having, suspected of having, or at risk of developing, a complement-mediated disorder (e.g., lupus nephritis, dense deposit disease, C3 glomerulonephritis, IgA nephropathy, membranous nephropathy, COPD, or asthma). Any suitable methods for obtaining the biological samples can be employed.

The term "epitope" is known in the art and refers to the specific part of the antigen that is recognized by an antibody. The term "neoepitope" refers to a new epitope which is formed due to altered transcription, translation, post-transcriptional modification, post-translational modification, proteolytic processing, or aggregation. Accordingly, as used herein in relation to C3a, a "neoepitope" refers to a new epitope which is formed by proteolytic processing of C3 by C3 convertase.

As used herein the term "Fluorescence Resonance Energy Transfer", also knowns as "Förster Resonance Energy Transfer" or "FRET", refers to an energy transfer mechanism occurring between two fluorescent molecules.

As used herein, the term "fluorophore" refers to a chemical compound, which when excited by exposure to a particular wavelength of light, emits light at a different wavelength. As used herein, the term "fluorophore" refers to any molecule known in the art that can be used for FRET, including dyes, fluorescent proteins, and quantum dots.

As used herein, the term "excitable distance" refers to the distance at which FRET can occur between a donor and an acceptor molecule, typically when they are within about 10-100 Å of each other.

As used herein, a "FRET pair" refers to two antibodies that bind within an excitable distance and are labeled with fluorophores that have overlapping donor emission and acceptor absorption spectrums and suitable dipole orientation.

As used herein, the terms "label" or "labeled" refers to the incorporation of a detectable moiety (e.g., a fluorophore) on the antibody. The label may be direct (i.e., a primary label) or indirect (i.e., a secondary label) and can be visualized and/or measured or otherwise identified using a detectable signal.

Other features and advantages of the present disclosure will be apparent from the following description, examples, and claims.

II. Antibodies Against C3 and C3a

Fluorophore labeled antibodies are required for FRET detection of C3 and C3a. Antibodies and antigen binding fragments thereof may be generated according to established hybridoma and recombinant procedures. Suitable methods for producing an antibody (e.g., an anti-C3, anti-C3a, or anti-C3b antibody) or antigen-binding fragments thereof may be obtained according to established hybridoma and recombinant procedures as previously disclosed (see, e.g., U.S. Pat. Nos. 7,427,665; 7,435,412; and 7,408,041). For example, a process for the production of an antibody disclosed herein includes culturing a host (e.g., *E. coli* or a mammalian cell), which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic, for example bicistronic, DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g., fetal calf serum), or trace elements and growth sustaining supplements (e.g., feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast, plant, or mammalian cell cultivation are known in the art and include homogeneous suspension culture (e.g., in an airlift reactor or in a continuous stirrer reactor), and immobilized or entrapped cell culture (e.g., in hollow fibers, microcapsules, on agarose microbeads or ceramic cartridges).

Large quantities of the desired antibodies can also be obtained by multiplying mammalian cells in vivo. For this purpose, cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristine. After one to two weeks, ascitic fluid is taken from the animals.

Techniques for purification of therapeutic antibodies to pharmaceutical grade are well known in the art. For example, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g., affinity chromatography with a one or more surface polypeptides derived from a CLL cell line according to this disclosure, or with Protein-A or G.

Other techniques for generating antibodies are discussed in, for example, Kohler and Milstein, (1975) *Nature* 256: 495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules is described in the above references and also in, for example WO97/08320; U.S. Pat. Nos. 5,427,908; 5,508,717; Smith (1985) *Science*, Vol. 225:1315-1317; Parmley and Smith (1988) *Gene* 73:305-318; De La Cruz et al. (1988) *J. Biol. Chem.*, 263:4318-4322; U.S. Pat. Nos. 5,403,484; 5,223,409; WO88/06630; WO92/15679; U.S. Pat. Nos. 5,780,279; 5,571,698; 6,040,136; Davis et al. (1999) *Cancer Metastasis Rev.*, 18(4):421-5; Taylor, et al. (1992) *Nucleic Acids Research* 20:6287-6295; Tomizuka et al. (2000) *Proc. Nat. Academy of Sciences USA* 97(2): 722-727 (the contents of each are incorporated herein by reference).

Anti-C3, C3a, and C3b antibodies (or VH/VL domains derived therefrom) suitable for use in the invention can be generated using the methods described above or other methods known in the art. Alternatively, art recognized or commercially available antibodies can be used. In one embodiment, at least one of the first and second antibodies comprises the heavy chain CDR1, CDR2, and CDR3 amino acid sequences set forth in SEQ ID NOs: 1, 2, and 3, respectively, and the light chain CDR1, CDR2, and CDR3 amino acid sequences set forth in SEQ ID NOs: 4, 5, and 6, respectively. In another embodiment, at least one of the first and second antibodies comprises the heavy chain variable region amino acid sequence set forth in SEQ ID NO: 7 and the light chain variable region amino acid sequence set forth in SEQ ID NO: 8. In yet another embodiment, at least one of the first and second antibodies comprises the heavy chain amino acid sequence set forth in SEQ ID NO: 9 and the light chain amino acid sequence set forth in SEQ ID NO: 10. In another embodiment, at least one of the first and second antibodies binds to an epitope recognized by an antibody having the heavy chain variable region comprising the amino acid sequence of SEQ ID NO: 7 and a light chain variable region comprising the amino acid sequence of SEQ ID NO: 8. Antibodies that compete with any of these antibodies for binding to C3, C3a, or C3b can also be used.

Antibodies can be labeled (e.g., with a fluorophore) using known techniques and reagents. For example, antibody labeling kits are available from ThermoFisher Scientific (Waltham, MA), Cisbio (Bedford, MA), PerkinElmer, Inc. (Waltham, MA), and Abcam (Cambridge, UK). Generally, labeling includes covalently attaching the label (e.g., fluorophore) to the antibody. Selection of fluorophore labels for FRET is discussed further below.

III. Fluorescence Resonance Energy Transfer (FRET)

To detect labeled antibodies bound to C3 and C3a, Fluorescence Resonance Energy Transfer (FRET) is used. FRET is based on the transfer of energy occurs between a FRET pair: a fluorescent donor molecule and a fluorescent acceptor molecule positioned within an excitable distance with overlapping donor emission and acceptor absorption spectrums and suitable dipole orientation. The donor is excited at its specific fluorescence excitation wavelength and transfers the fluorescent energy to the acceptor molecule. The donor then returns to the ground state.

Any variation of FRET can be used in the methods described herein. For example, time-resolved FRET (TR-FRET) can be used. TR-FRET generally employs a long-lifetime donor species (e.g., terbium chelate, samarium, europium, terbium, and dysprosium) and a suitable acceptor species (e.g., fluorescein, allophycocyanin, and d2 dye), wherein the TR-FRET value is determined as a ratio of the FRET-specific signal produced by the acceptor to that of the signal produced by the donor. In one embodiment, the FRET is time-resolved fluorescence energy transfer (TR-FRET).

The FRET pair may include labeled primary antibodies or labeled secondary antibodies. In one embodiment, one of the first and second antibodies is labeled with a donor fluorophore, and the other of the first and second antibodies is labeled with an acceptor fluorophore. Donor-acceptor pairs usable for studying the FRET phenomena are known in the art (See e.g., Lakowicz, Principles of fluorescence spectroscopy, 2nd edition, (1999) Springer). Suitable donor fluorophores include terbium cryptate dye. Suitable acceptor fluorophores include d2 dye. In one embodiment, the donor fluorophore is excited at 300-600 nm. In another embodiment, the signal from the donor fluorophore is measured at 400-700 nm. In another embodiment, the signal from the acceptor fluorophore is measured at 400-700 nm. In one embodiment, the antibodies bind within 10-100 Å of each other. In another embodiment, the antibodies bind within 50-90 Å of each other.

The FRET signal can be used to detect or quantify a protein in a biological sample (e.g., C3) by comparing the FRET signal from the biological sample to a standard curve produced using FRET signals from the protein at known concentrations. Changes in the FRET signal over a time course can be used to monitor changes in the amount of C3 or C3a within a human patient over time.

EXAMPLES

The following examples are merely illustrative and should not be construed as limiting the scope of the disclosure in any way as many variations and equivalents will become apparent to those skilled in the art upon reading the present disclosure.

Example 1: Detection of C3a in a Sample that Includes C3 and C3b Using FRET

Figure 1B:
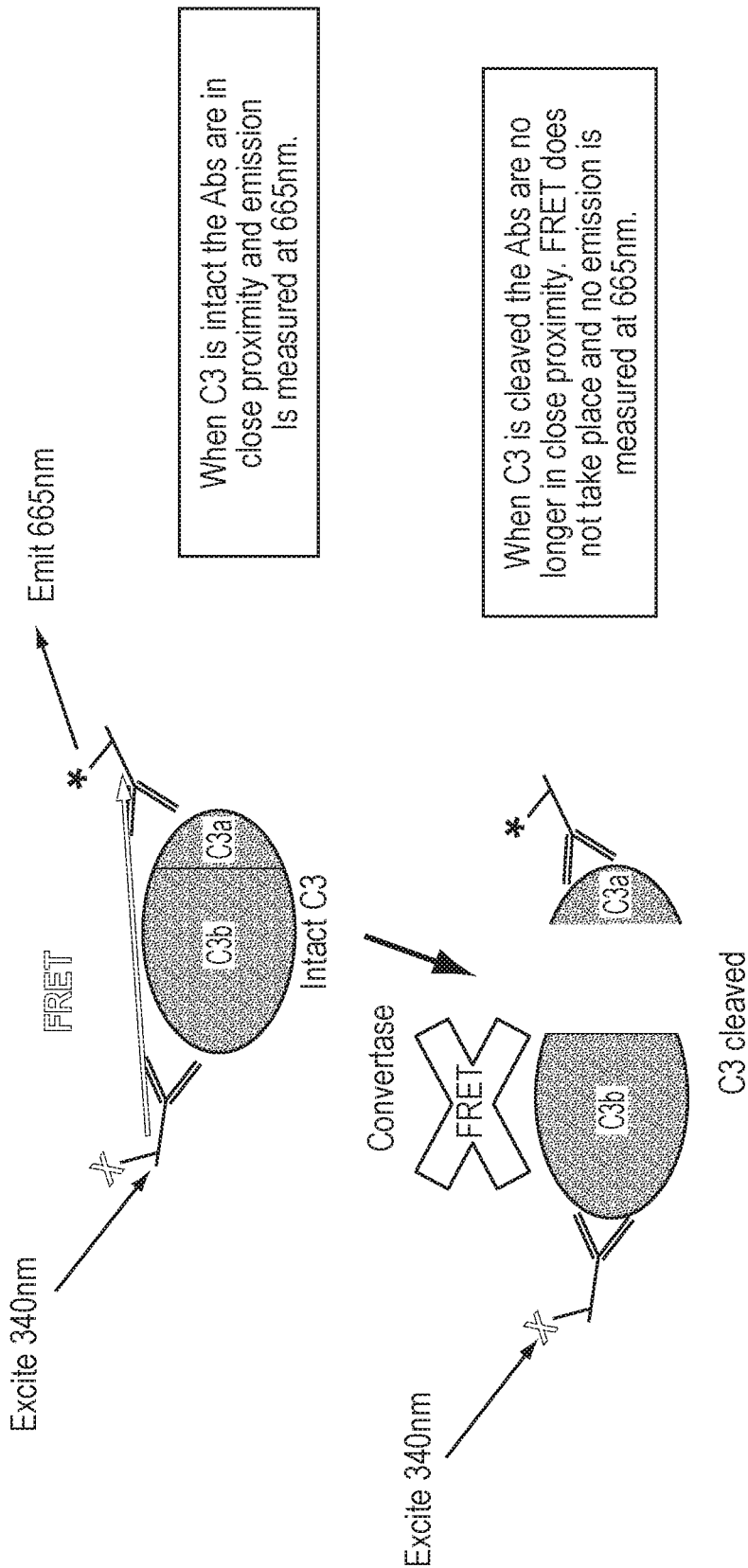
Figure 2A:
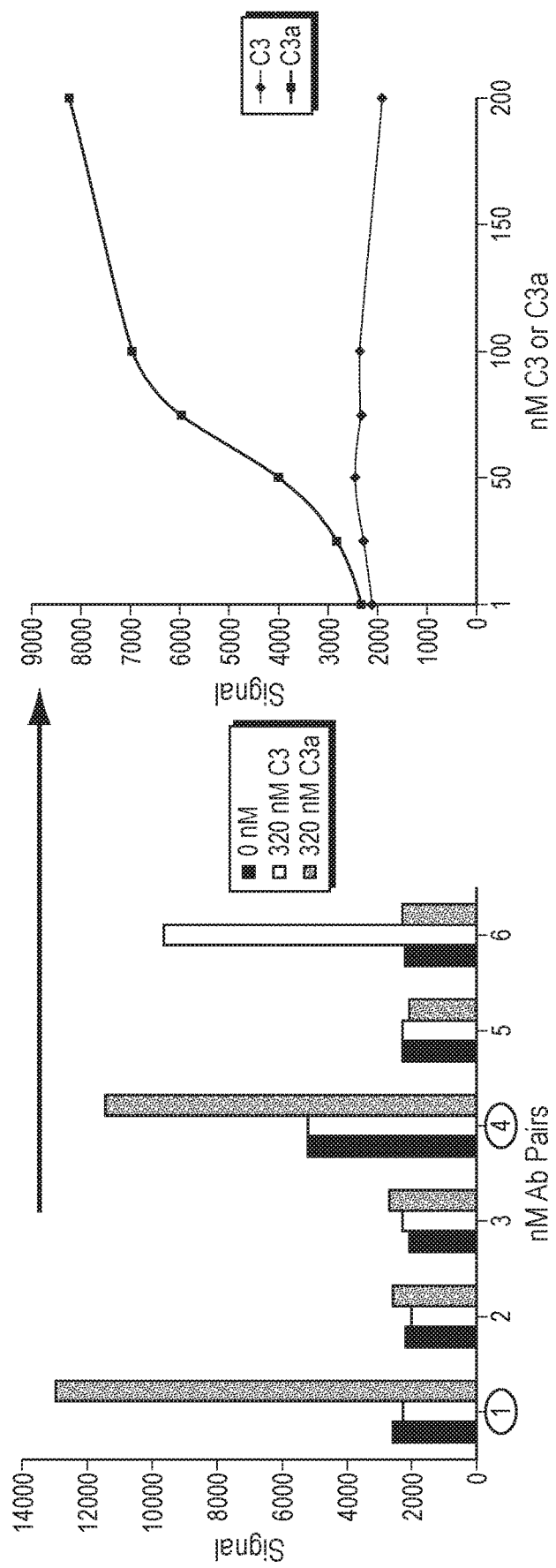
FIGS. 2A and 2B show antibody pair selection for FRET assay to detect C3a and C3, respectively.
Figure 2B:
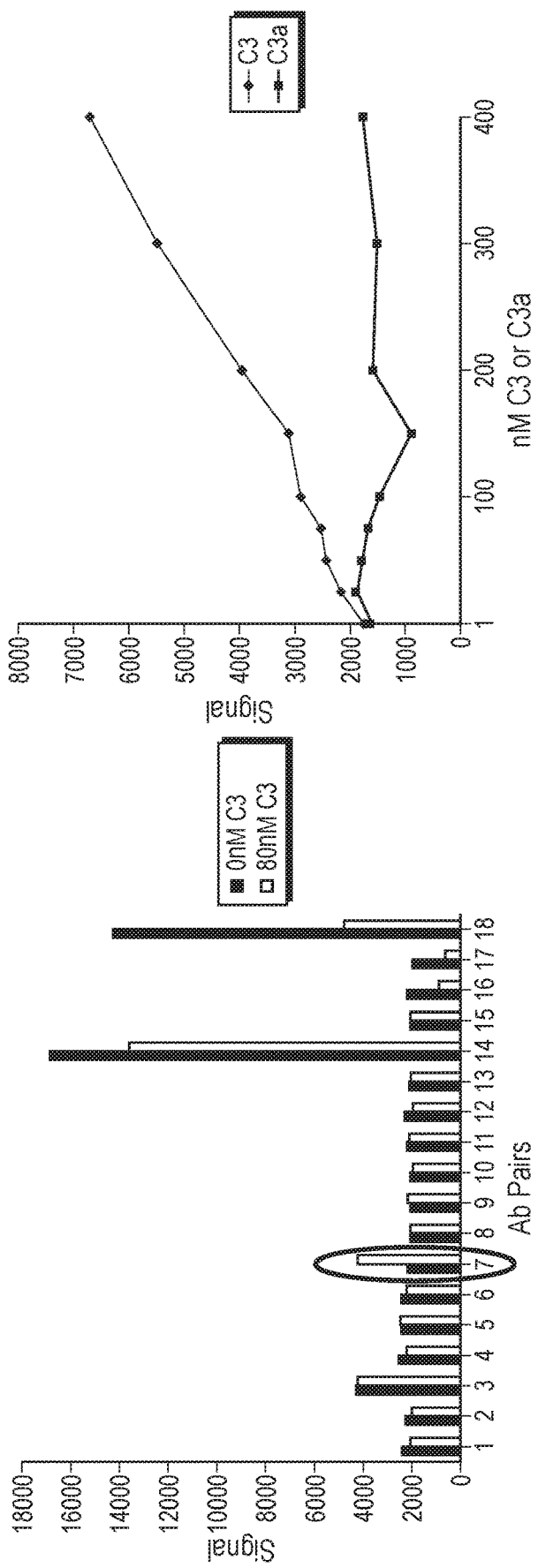

The FRET assay can be used to detect C3a or C3, as well as measure the consumption of C3 by measuring the gain of FRET signal or the loss of FRET signal in a sample, as shown schematically in FIGS. 1A and 1B, respectively. However, antibodies must be selected that can distinguish between transient populations of C3, C3a, and C3b proteins. Antibody pairs were generated and commercially purchased, and tested to find pairs that bound to epitopes within an excitable distance, but did not interact with each other. FIG. 2A shows antibody pairs that were tested for C3a detection and gain of FRET signal assays. Pairs were also identified for C3 detection and loss of FRET signal assays, as shown in FIG. 2B.

Antibodies were labeled using a d2 labeling kit and a terbium cryptate labeling kit from Cisbio (Cat. #62D2DPEA and 62TBSPEA). The antibody which was specific for the C3a neoepitope (HM2074) was purchased from Hycult (Cat. #HM2074-IA—without albumin). The other C3a antibody (YHP133) was synthesized and purified according to standard procedures. The C3a detection antibodies were labeled according to Cisbio's protocol. Briefly, the antibodies were buffer exchanged using Zeba spin desalt columns (Pierce Thermo Cat. #28382). The HM2074 antibody was buffer exchanged into 50 mM Phosphate buffer (pH 8.0) to be labeled with terbium cryptate dye. The YHP133 antibody was buffer exchanged into 50 mM carbonate buffer (pH 9.0) to be labeled with d2 dye. The antibody concentrations were determined, adjusted appropriately according to Cisbio's protocol and added to the Cisbio vials with the appropriate dye. The vials were vortexed and incubated. During incubation the provided Cisbio column was equilibrated with 10 mls of the provided elution buffer. After incubation antibodies were added to their respective columns and separated from unlabeled dye molecules. The fraction which contained the labeled dye was collected according to the protocol. The antibody concentrations were determined using the Nano 1000 droplet method and the ratio of dye molecules per antibody was determined. Tween-20 and bovine serum albumin (BSA) were added at a final concentration of 0.1% each. Antibodies were aliquoted and stored at −20° C.

Figure 3:
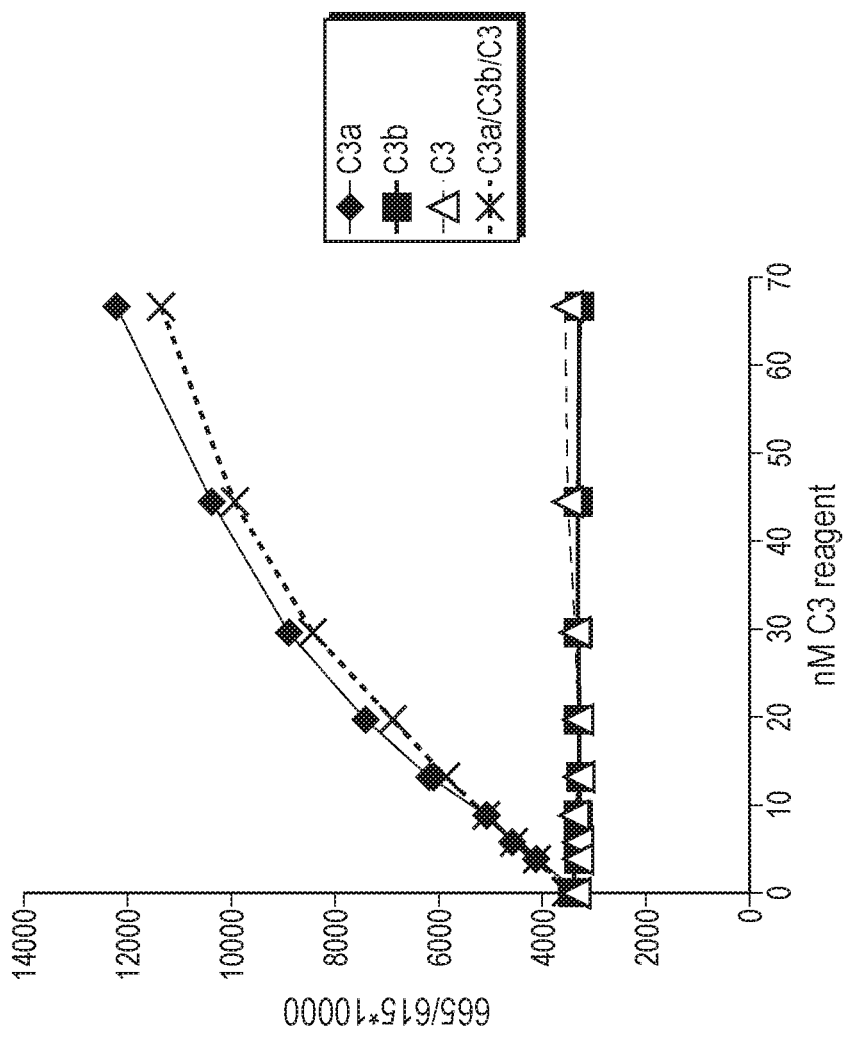
FIG. 3 shows detection of purified C3a in a sample that includes intact C3 and C3b using fluorescence resonance energy transfer (FRET).

Labeled antibodies were then used to detect C3a in a sample that also contained intact C3 and C3b fragments. FIG. 3 shows FRET detection over a titration of C3 reagents. For the detection assay, complement C3 and fragments C3a and C3b were purchased from Complement Technologies (cat #A113c, A118, and A114, respectively). They were aliquoted and stored at −80° C. Each complement protein was titrated individually or as a mixture in assay buffer (10 mM HEPES pH 7.4, 0.1% BSA) at final concentrations of 66.6 nM serially diluted. Detection antibodies were combined in assay buffer to make a C3a detection mixture at final concentrations of 50 nM each in assay. Then, 15 µl of the appropriate C3 reagent was added to the appropriate wells of a white 384 well Optiplate (Perkin Elmer Cat. #600-7290). To each well, 15 µl antibody detection mix was then added. The plate was spun at 4000 RPM for 20 seconds and read on a Paradigm Spectramax instrument using the Cisbio htrf cartridge (excite at 340 nm and emit at 615 nm and 665 nm). The plate was read periodically and the signal calculated by dividing the 665 signal by the 615 signal and multiplying by 10000.

As shown in FIG. 3, C3a was detected at similar levels in samples containing C3a alone or in combination with intact C3 and the C3b fragment. The FRET assay did not detect C3 or C3b and, accordingly, can be used to reliably distinguish between C3, C3a, and C3b in mixed samples.

Example 2: FRET Detection of Real-Time C3a Production

A major advantage to the FRET assay is that, unlike other methods for protein detection, it can be used over time to follow the consumption of C3 and production of C3a. Real-time C3a production is shown in FIGS. 4A and 4B.

Figures 4A, 4B:
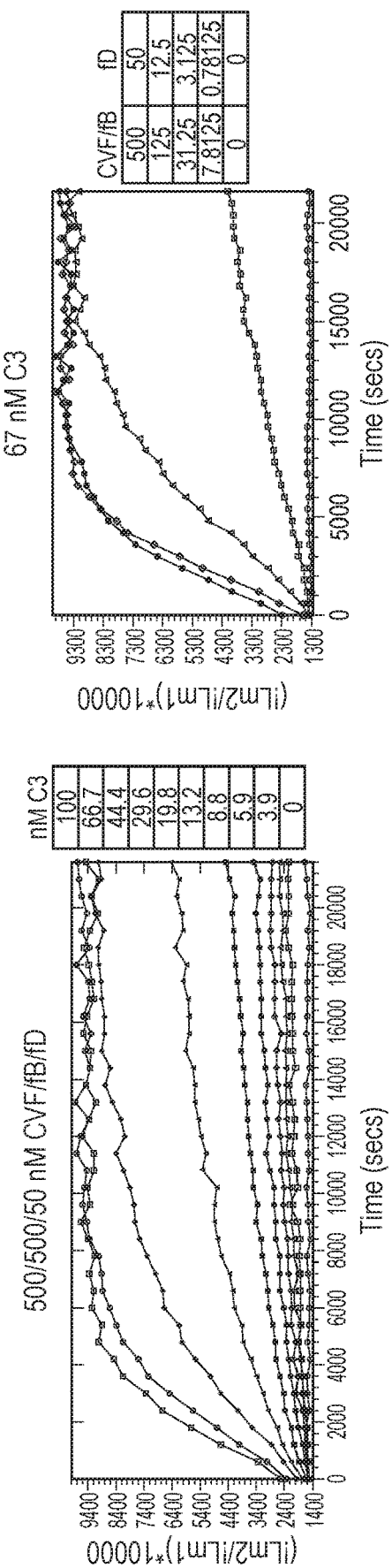
FIGS. 4A and 4B are graphs showing C3 cleavage over a time course using FRET to detect C3a accumulation.

To follow C3a production, a convertase mix consisting of cobra venom factor (CVF), factor B (fB), and factor D (fD) was made in assay buffer to reach final concentrations of 500, 500, and 50 nM, respectively, in the reaction, as shown in FIG. 4A. CVF, fB, and fD were purchased from Complement Technologies (Cat. #A150, A135, and A136, respectively). After fB binds to CVF, it is cleaved by fD such that it can then cleave C3 and generate C3a.

A C3a detection antibody mix was made in assay buffer consisting of HM2074 and YHP133 antibodies to reach final concentrations of 50 nM each in the reaction. Complement C3 substrate was titrated in assay buffer to reach final concentrations of 100 nM serially diluted in the reaction. Next, 10 µl of assay buffer was added to each well of a white 384 well Optiplate. This was followed by adding 10 µl Convertase mix, 10 µl of Magnesium Chloride at a final concentration of 30 mM, and 10 µl of the antibody detection mix to each well. Lastly, 10 µl of titrated C3 substrate was added to begin the reaction. The plate was spun at 4000 RPM for 20 seconds and read every 10 minutes on the Spectramax Flexstation 3 instrument at 340 nm excite and 615/665 nm emission. The signal was calculated by dividing the 665 signal by the 615 signal and multiplying by 10000.

The data in FIG. 4A shows that as time increased, C3a increased, as detected by an increase in FRET signal. The signal of C3a formed titrated with the amount of C3 added. Further, as shown in FIG. 4B, the signal of C3a formed was dependent on the amount of convertase added, with 125/125/12.5 nM of the CVF/fB/fD mix providing similar C3a signal as 500/500/50 nM. This occurred as a result of C3 cleavage into C3a and C3b products. Therefore, the assay was able to accurately measure the production of C3a in real time.

Example 3: Detection of C3a in Human Serum and Urine Using FRET

The FRET assay provides a method to detect C3a levels in human biological samples, such as serum or urine. This can be used, for example, for diagnostic purposes, to follow patient conditions or response to treatment over time, or to stratify patient populations in clinical trials.

Figure 5:
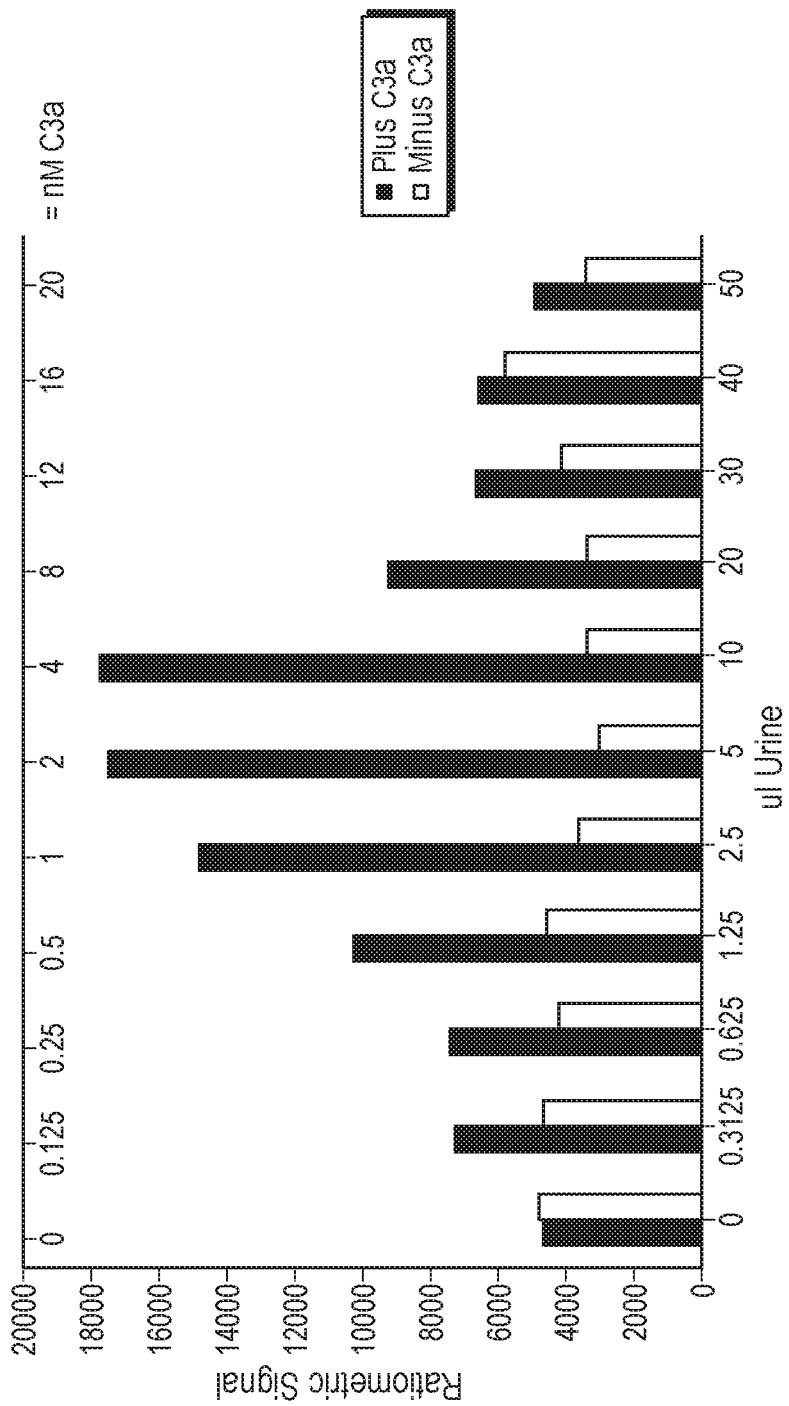
FIG. 5 shows detection of varying amounts of C3a in a titration of human urine.

To determine range of C3a detection in urine samples, the FRET signal was measured while titrating urine with and without C3a (FIG. 5). Human urine was titrated (0.52%-83.3% total volume) and 50 µl+/−titrated C3a (0.125-20 nM) was added to a white 384 well Optiplate. To each well, 10 µl of antibody mix including 0.5 nM and 7.5 nM donor and acceptor antibodies, respectively, was added. The plate was spun at 4000 RPM for 20 seconds and read on a Paradigm Spectramax instrument using the Cisbio htrf cartridge (excite at 340 nm and emit at 615 nm and 665 nm). The plate was read periodically and the signal calculated by dividing the 665 signal by the 615 signal and multiplying by 10000. The graph in FIG. 5 shows a strong FRET signal at varying concentrations of C3a.

Figure 6A:
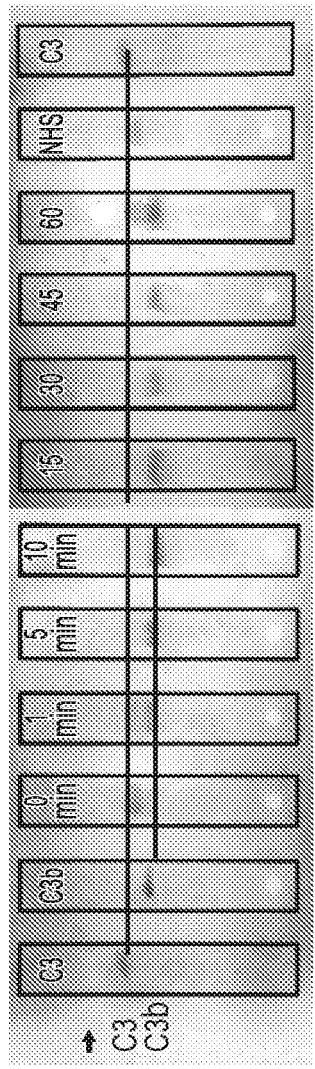
FIG. 6A is a gel showing time dependent cleavage of C3 in human serum.
Figure 6B:
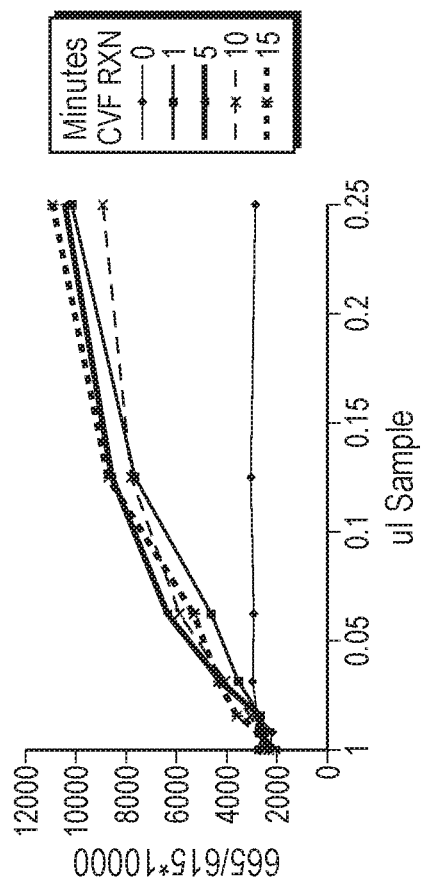
FIG. 6B shows FRET detection of C3a in human serum over a time course.

For detection in human serum, C3a production was followed over a time course using immunofixation electrophoresis and the FRET assay, as shown in FIGS. 6A and 6B, respectively. Cobra Venom Factor (CVF—Cat. #A150) was added to Normal Human Serum (NHS Cat. #HMSRM-Comp—Bioreclamation LLC.) at 37° C. in order to cleave endogenous C3 and form C3b and C3a. Then, 20 µl of sample was removed at appropriate times and the reaction stopped in 20 µl GVBS, (Gelatin Veronal Buffered Saline) 10 mM MgCl2, 10 mM EDTA and placed on ice. Samples were further diluted 12 fold with 0.85% saline and 3 µl was run in immunofixation electrophoresis (IFE—Helena Laboratories). The gel was blotted with a polyclonal antibody to C3 (detects C3 AND C3b—MP bio) and stained with Acid blue (FIG. 6A). Standards C3 (Cat. #A113c) and C3b (Cat. #A114) were purchased from Complement Technologies and included on the gel as controls.

Figure 7:
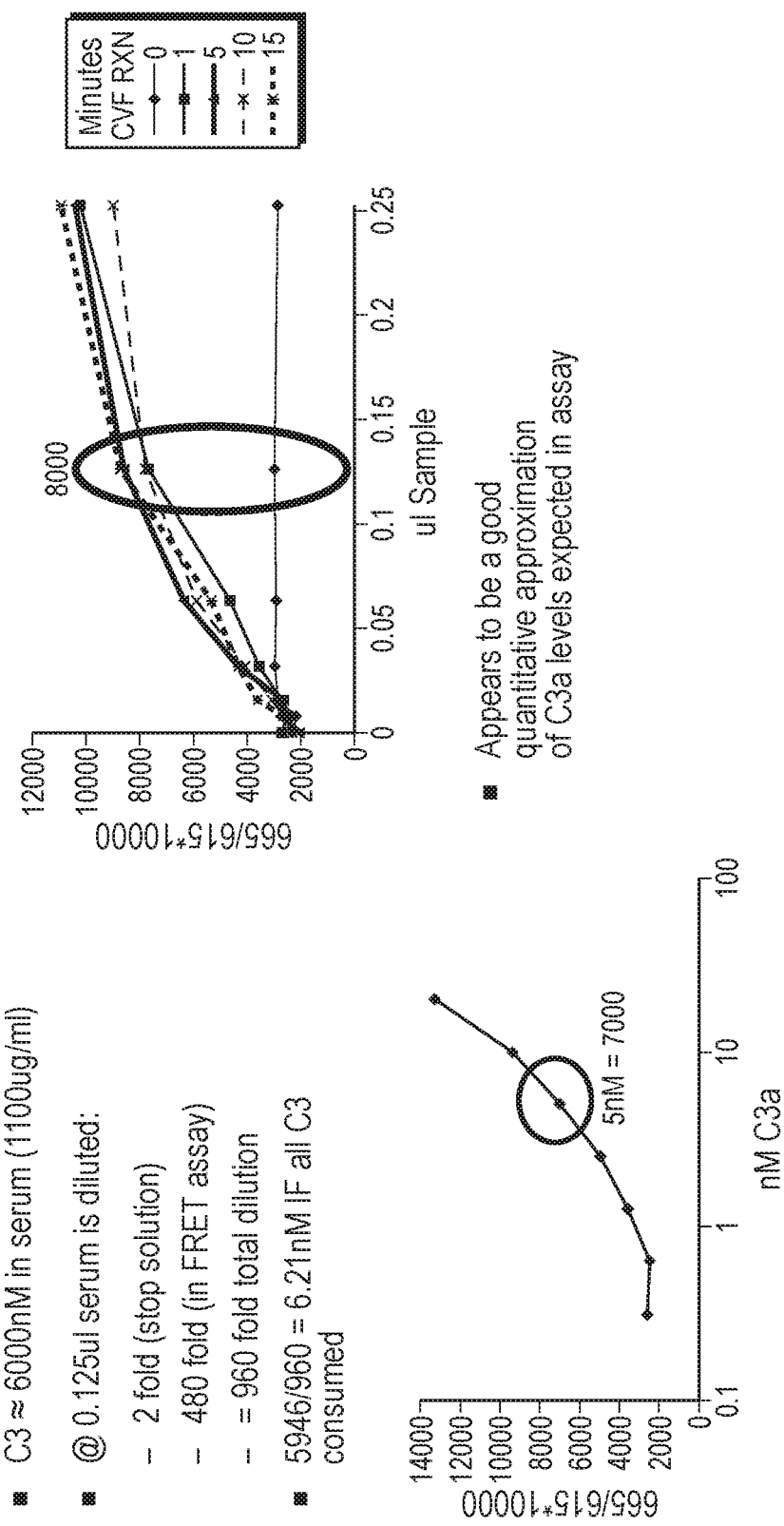
FIG. 7 shows quantification of C3 in human serum by comparison of C3a FRET signal to a standard curve.

The samples generated in the above experiment were diluted, titrated, and 30 µl added to a 384 well white Optiplate. Alternatively, C3a from Complement Technologies (Cat. #A118) was titrated in separate wells for a standard curve. Next, 30 µl of C3a detection antibodies (HM2074 and YHP133) were added at 0.5 nM and 0.64 nM, respectively. The plate was spun at 4000 RPM for 20 seconds and read on a Paradigm Spectramax instrument using the Cisbio htrf cartridge (excite at 340 nm and emit at 615 nm and 665 nm). The plate was read periodically and the signal calculated by dividing the 665 signal by the 615 signal and multiplying by 10000 (FIG. 6B). The FRET signal was then used to calculate the amount of C3a in the sample, as shown in FIG. 7.

The gel in FIG. 6A shows the time dependent consumption of C3, as the band for C3 decreases in intensity and the band for C3b increases in intensity over time. The FRET data for C3a production, in FIG. 6B, is in agreement with the low throughput gel data. Both sets of data show that C3 consumption increases over time, producing C3a and C3b. This demonstrated that the FRET assay can be used to accurately and efficiently measure C3a production for high throughput assays.

SEQUENCE LISTING
amino acid sequence of heavy chain CDR1 of C3a antibody YHP133
SEQ ID NO: 1
GFNIKDSLIH amino acid sequence of heavy chain CDR2 of C3a antibody YHP133
SEQ ID NO: 2
WIDPDDGETKYAPKFQD amino acid sequence of heavy chain CDR3 of C3a antibody YHP133
SEQ ID NO: 3
RSGEGYFDY amino acid sequence of light chain CDR1 of C3a antibody YHP133
SEQ ID NO: 4
RASQSISDYLH amino acid sequence of light chain CDR2 of C3a antibody YHP133
SEQ ID NO: 5
ASQSISG amino acid sequence of light chain CDR3 of C3a antibody YHP133
SEQ ID NO: 6
QNGHSFPLT amino acid sequence of heavy chain variable region of C3a antibody YHP133
SEQ ID NO: 7
EVQLQQSGAELVRPGASVKLSCTASGFNIKDSLIHWVKQRPEQGLEWIG

WIDPDDGETKYAPKFQDKATITADTSSNTAYLQFSSLTSEDTAIYYCAG

RSGEGYFDYWGQGTTVTVSS amino acid sequence of light chain variable region of C3a antibody YHP133
SEQ ID NO: 8
DIVMTQSPATLSVTPGDRVSLSCRASQSISDYLHWYQQKSHESPRLLIK

YASQSISGIPSRFSGSGSGSDFTLSINSVEPEDVGVYYCQNGHSFPLTF

GAGTKVEIK amino acid sequence of heavy chain of C3a antibody YHP133
SEQ ID NO: 9
EVQLQQSGAELVRPGASVKLSCTASGFNIKDSLIHWVKQRPEQGLEWIG

WIDPDDGETKYAPKFQDKATITADTSSNTAYLQFSSLTSEDTAIYYCAG

RSGEGYFDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKRVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKS

LSLSPGK amino acid sequence of light chain of C3a antibody YHP133
SEQ ID NO: 10
DIVMTQSPATLSVTPGDRVSLSCRASQSISDYLHWYQQKSHESPRLLIK

YASQSISGIPSRFSGSGSGSDFTLSINSVEPEDVGVYYCQNGHSFPLTF

GAGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

I claim:

1. A method of detecting C3a in a biological sample, the method comprising:
   (a) incubating the biological sample with a first and second antibody that bind to human C3a, wherein the first, but not the second, antibody binds to a neoepitope, and wherein the antibodies are FRET pairs; and
   (b) performing fluorescence resonance energy transfer (FRET) to detect the FRET signal, thereby detecting C3a in the biological sample,
   wherein the first antibody comprises heavy chain CDR1, CDR2, and CDR3 amino acid sequences as set forth in SEQ ID NOs: 1, 2, and 3, respectively, and light chain CDR1, CDR2, and CDR3 amino acid sequences as set forth in SEQ ID NOs: 4, 5, and 6, respectively.

2. The method of claim 1, wherein the first antibody comprises a heavy chain variable region amino acid sequence as set forth in SEQ ID NO: 7 and a light chain variable region amino acid sequence set forth in SEQ ID NO: 8.

3. A method of detecting C3 in a biological sample, the method comprising:
   (a) incubating the biological sample with a first and second antibody that bind to human C3, wherein the first antibody also binds to an epitope on C3a and the second antibody also binds to an epitope on C3b, and wherein the antibodies are FRET pairs; and
   (b) performing fluorescence resonance energy transfer (FRET) to detect the FRET signal, thereby detecting C3 in the biological sample,
   wherein the first antibody comprises heavy chain CDR1, CDR2, and CDR3 amino acid sequences as set forth in SEQ ID NOs: 1, 2, and 3, respectively, and light chain CDR1, CDR2, and CDR3 amino acid sequences as set forth in SEQ ID NOs: 4, 5, and 6, respectively.

4. The method of claim 1 or 3, further comprising repeating steps (a) and (b) over a time course.

5. The method of claim 1 or 3, further comprising (c) quantifying the amount of C3a or C3 in the biological sample.

6. The method of claim 5, further comprising repeating steps (a), (b), and (c) over a time course.

7. The method of claim 1 or 3, wherein one of the first and second antibodies is labeled with a donor fluorophore and the other of the first and second antibodies is labeled with an acceptor fluorophore.

8. The method of claim 7, wherein the donor fluorophore is terbium cryptate dye and/or is excited at 300-600 nm.

9. The method of claim 7, wherein the acceptor fluorophore is d2 dye.

10. The method of claim 7, wherein the signal from the donor fluorophore is measured at 400-700 nm and/or the signal from the acceptor fluorophore is measured at 400-700 nm.

11. The method of claim 1 or 3, wherein the antibodies bind within 10-100 Å of each other.

12. The method of claim 1 or 3, wherein the FRET is time-resolved fluorescence energy transfer (TR-FRET).

13. The method of claim 1 or 3, wherein prior to step (a), the biological sample is treated with a convertase and/or cobra venom factor, factor B, and factor D.

14. The method of claim 1 or 3, wherein the biological sample is human serum, plasma, cell supernatant, cell lysate, or urine.

15. The method of claim 14, wherein the biological sample is from a human patient suffering from a complement-related disease, lupus nephritis, dense deposit disease, C3 glomerulonephritis, IgA nephropathy, membranous nephropathy, COPD, or asthma.

16. The method of claim 3, wherein the first antibody comprises a heavy chain variable region amino acid sequence as set forth in SEQ ID NO: 7 and a light chain variable region amino acid sequence set forth in SEQ ID NO: 8.

17. A method of detecting C3a in a biological sample, the method comprising:
   (a) incubating the biological sample with a first and second antibody that bind to human C3a, wherein the first, but not the second, antibody binds to a neoepitope, and wherein the antibodies are FRET pairs; and
   (b) performing fluorescence resonance energy transfer (FRET) to detect the FRET signal, thereby detecting C3a in the biological sample;
   (c) quantifying the amount of C3a in the biological sample; and
   (d) repeating steps (a), (b), and (c) sequentially over a time course,
   wherein the first antibody comprises heavy chain CDR1, CDR2, and CDR3 amino acid sequences as set forth in SEQ ID NOs: 1, 2, and 3, respectively, and light chain CDR1, CDR2, and CDR3 amino acid sequences as set forth in SEQ ID NOs: 4, 5, and 6, respectively.

18. The method of claim 17, wherein the first antibody comprises a heavy chain variable region amino acid sequence as set forth in SEQ ID NO: 7 and a light chain variable region amino acid sequence set forth in SEQ ID NO: 8.

19. A method of detecting C3 in a biological sample, the method comprising:
   (a) incubating the biological sample with a first and second antibody that bind to human C3, wherein the first antibody binds to an epitope on C3a and the second antibody binds to an epitope on C3b, and wherein the antibodies are FRET pairs; and
   (b) performing fluorescence resonance energy transfer (FRET) to detect the FRET signal, thereby detecting C3 in the biological sample;
   (c) quantifying the amount of C3 in the biological sample by comparing the FRET signal to a standard curve; and
   (d) repeating steps (a), (b), and (c) sequentially over a time course,
   wherein the first antibody comprises heavy chain CDR1, CDR2, and CDR3 amino acid sequences as set forth in SEQ ID NOs: 1, 2, and 3, respectively, and light chain CDR1, CDR2, and CDR3 amino acid sequences as set forth in SEQ ID NOs: 4, 5, and 6, respectively.

20. The method of claim 19, wherein the first antibody comprises a heavy chain variable region amino acid sequence as set forth in SEQ ID NO: 7 and a light chain variable region amino acid sequence set forth in SEQ ID NO: 8.

* * * * *